(12) United States Patent
Austin et al.

(10) Patent No.: US 7,454,880 B1
(45) Date of Patent: Nov. 25, 2008

(54) PERSONALIZED MEDICATION PACKAGING

(75) Inventors: Paul R. Austin, Webster, NY (US); Kristine A. German, Webster, NY (US)

(73) Assignee: Xerox Corporation, Stamford, CT (US)

( * ) Notice: Subject to any disclaimer, the term of this patent is extended or adjusted under 35 U.S.C. 154(b) by 0 days.

(21) Appl. No.: 11/807,962

(22) Filed: May 31, 2007

(51) Int. Cl.
*B65B 6/02* (2006.01)
*B42D 15/00* (2006.01)

(52) U.S. Cl. .......................... 53/411; 53/131.2; 700/216

(58) Field of Classification Search ................... 53/411, 53/415, 467, 131.2, 135.1, 281, 286; 700/216; 283/900, 75, 89
See application file for complete search history.

(56) References Cited

U.S. PATENT DOCUMENTS

| | | | | |
|---|---|---|---|---|
| 5,502,944 | A * | 4/1996 | Kraft et al. ...................... 53/55 |
| 6,021,392 | A * | 2/2000 | Lester et al. .................... 705/2 |
| 6,522,945 | B2 * | 2/2003 | Sleep et al. .................. 700/225 |
| 6,688,075 | B2 * | 2/2004 | Cristina ........................... 53/55 |
| 6,715,265 | B2 * | 4/2004 | Franzaroli .................... 53/435 |
| 6,721,762 | B1 * | 4/2004 | Levine et al. ............. 707/104.1 |
| 6,779,319 | B2 * | 8/2004 | Smith et al. ................... 53/493 |
| 6,892,512 | B2 * | 5/2005 | Rice et al. ..................... 53/445 |
| 6,909,936 | B2 * | 6/2005 | Franzaroli .................... 700/159 |
| 6,938,397 | B2 * | 9/2005 | Miller ........................... 53/461 |
| 6,983,579 | B2 * | 1/2006 | Rice et al. ..................... 53/494 |
| 7,048,141 | B2 * | 5/2006 | Abdulhay et al. ............... 221/3 |
| 7,061,831 | B2 * | 6/2006 | De La Huerga ............... 368/10 |
| 7,080,755 | B2 | 7/2006 | Handfield et al. |
| 7,213,721 | B2 * | 5/2007 | Abdulhay et al. ............... 221/3 |
| 2002/0104293 | A1 * | 8/2002 | Armington et al. ............ 53/472 |
| 2004/0064215 | A1 * | 4/2004 | Greeven et al. ............. 700/235 |
| 2005/0043674 | A1 * | 2/2005 | Blair et al. ..................... 604/66 |
| 2005/0256830 | A1 * | 11/2005 | Siegel et al. .................... 707/1 |
| 2006/0107623 | A1 * | 5/2006 | Rice et al. ...................... 53/494 |
| 2006/0163103 | A1 | 7/2006 | Adler et al. |
| 2006/0163110 | A1 | 7/2006 | Adler et al. |
| 2006/0163869 | A1 | 7/2006 | Adler et al. |

* cited by examiner

*Primary Examiner*—Paul R Durand
(74) *Attorney, Agent, or Firm*—Carter, DeLuca, Farrell & Schmidt, LLP

(57) ABSTRACT

A system for personalized packaging of prescription medication includes a processing device having a CPU and a user interface. The user interface is configured to receive input data related to at least one type of medication to be packaged, wherein the user interface communicates the input data to the CPU for processing. A dispensing system is in communication with the processing device, wherein the dispensing system is configured to be pre-supplied with the at least one type of medication and to dispense the at least one type of medication based on the input data communicated from the CPU to the dispensing system. Also included in the system is a printing system in communication with the processing device. A printing system is configured to generate a print of instructional data based on the input data communicated from the CPU to the printing system, wherein the print of instructional data includes data correspondingly related to the at least one type of medication dispensed by the dispensing system. A packaging system is in communication with the dispensing system and configured to seal the at least one type of medication dispensed from the dispensing system within the personalized packaging.

22 Claims, 4 Drawing Sheets

PERSONALIZED MEDICATION PACKAGING

BACKGROUND

The present disclosure relates generally to an integrated medicament packaging and labeling system and more specifically to a prescription medication packaging and labeling system which is designed to clearly provide information about the medicament in order to avoid misuse of the medicament.

Medicine is often prescribed in combination for today's therapies, and the regimes can be quite complex due to constraints on taking combinations of medications as well as constraints on when and how often medications must be taken. Many hospitalizations and numerous deaths are attributed to failure to follow the medical regimen accurately.

When medication regimes are complex, patient confusion can result in under use, over use, or taking pills at the wrong time. If medications are prescribed to more than one family member, health risks are compounded by the possibility of taking the wrong medication. The consequences of noncompliance may be fatal. Providing clear instruction for proper following of a medical regimen is paramount for helping the broadest range of patients.

SUMMARY

According to aspects illustrated herein, a system for personalized packaging of prescription medication includes a processing device having a CPU and a user interface. The user interface is configured to receive input data related to at least one type of medication to be packaged, wherein the user interface communicates the input data to the CPU for processing. A dispensing system is in communication with the processing device, wherein the dispensing system is configured to be pre-supplied with the at least one type of medication and to dispense the at least one type of medication based on the input data communicated from the CPU to the dispensing system. Also included in the system is a printing system in communication with the processing device. A printing system is configured to generate a print of instructional data based on the input data communicated from the CPU to the printing system, wherein the print of instructional data includes data correspondingly related to the at least one type of medication dispensed by the dispensing system. A packaging system is in communication with the dispensing system and configured to seal the at least one type of medication dispensed from the dispensing system within the personalized packaging.

In a further embodiment, a method packaging medication includes generating input data related to the medication to be packaged through a user interface in communication with a processing device, wherein the processing device includes a CPU configured to process the input data received from the user input, dispensing the medication from a dispensing system in bilateral communication with the processing device, the dispensing device being configured to receive the user input from the CPU, wherein the medication dispensed is based on the user input, generating a print of instructional data from a printing system in communication with the processing device, the printing system being configured to receive the user input from the CPU, wherein the print of instructional data is based on the user input, and packaging the dispensed medication through a packaging system in communication with the dispensing device, the packaging system being configured to package the medication dispensed from the dispensing system.

In another embodiment, a system for personalized packaging of medication includes a processing device having a user interface, the user interface being configured to receive input data related to at least one container of medication to be packaged. The at least one container of medication includes machine readable data related to the medication encoded thereon for monitoring by the processing device. A dispensing system having a machine readable memory device is in communication with the processing device, wherein the dispensing system is configured to be pre-supplied with the at least one container of medication and to dispense the at least one container of medication based on the input data communicated from the processing device to the dispensing system. The dispensing system further includes a scanning means for reading the machine readable data, wherein the machine readable data is stored in the machine readable memory device for communication to the processing device. A printing system is in communication with the processing device and is configured to generate a print of instructional data based on the input data communicated from the processing device to the printing system, wherein the print of instructional data includes data correspondingly related to the at least one container of medication dispensed by the dispensing system. A packaging system is in communication with the dispensing system and is configured to seal the medication from the at least one container of medication dispensed from the dispensing system within the personalized packaging, wherein the personalized packaging is configured for mated relation to the print of instructional data.

BRIEF DESCRIPTION OF THE DRAWINGS

Various embodiments of the present disclosure will be described herein below with reference to the figures wherein.

DETAILED DESCRIPTION

Figure 1:
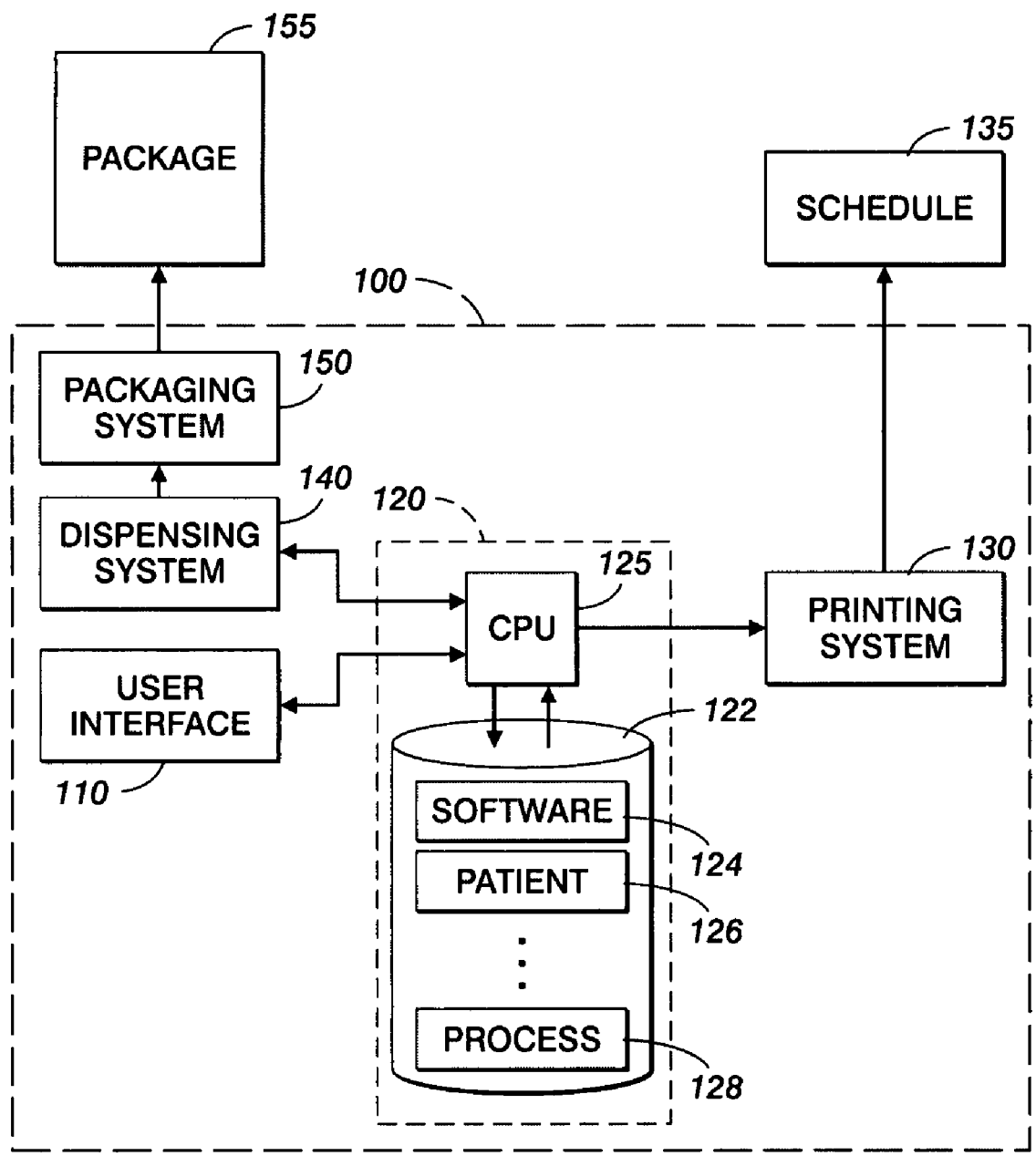
FIG. 1 shows a schematic representation of a personalized packaging system according to embodiments of the present disclosure.

Referring to FIG. 1 there is shown a personalized packaging system 100 according to embodiments of the present disclosure. Operation of the system is controlled by a processing device 120. The processing device 120 may be, for example, an electronic planner, a PDA, a computer, or the like. The processing device 120 includes a CPU 125 and a memory 122. The memory 122 is generic and may comprise RAM, ROM, CD-ROM, or other media of storage such as hard disk, magnetic tape, or the like. Other devices for accepting, capturing and storing data are well known and the above list should not be construed as exhaustive.

The memory 122 may contain system software 124, stored patient prescription files 126, and a packaging process 128 (discussed below). The system software 124, which is run by the CPU 125, may reside in ROM, RAM, or other units of storage. The system software 124 may include any well-known variable data printing application for generating a formatted layout of data in a printed format. It will also be appreciated that the memory 122 may be a shared or distributed resource among many processing devices (not shown in FIG. 1) in a networked configuration.

The processing device 120 is connected to a user interface 110, a printing system 130, and a medication dispensing system 140. The user interface 110 is generically labeled and encompasses a wide variety of such devices. These interface devices include touch screens, keyboards, and graphical user interfaces.

The dispensing system 140 is in bidirectional communication with the CPU 125. The dispensing system 140 is configured to be pre-supplied with various prescription pills and/or capsules (not explicitly shown) for dispensing and subsequent packaging by a packaging system 150 (discussed below). The user interface 110 receives input data from a user (e.g., a pharmacist, a pharmacy clerk, etc.) related to a patient's medication prescription. This input data is communicated to the CPU 125 which upon processing the input data, communicates the input data to the dispensing system 140 and the printing system 130 in a substantially simultaneous manner. Based on this input data received from the CPU 125, the dispensing system 140 dispenses medication and the printing system 130 generates a corresponding print 135 of instructional data related to the dispensed medication such as, for example, dosage, color images of the tablets and/or capsules, daily dose, patient name and address, doctor name and address, name and purpose of the medicament, etc., as will be discussed in further detail below. The dispensing system 140 may communicate back to the user interface 110 via the CPU 125 information such as, for example, medication inventory, dispensing system malfunctions, etc. It will also be appreciated that the dispensing system 140 may be a plurality of medicament dispensing devices (not shown in FIG. 1) configured to communicate with the processing device 120 in a networked configuration.

In embodiments of the present disclosure, the dispensing system 140 may include scanning means such as an optical scanner, a barcode reader, or the like for reading machine readable codes such as bar codes, data glyphs, etc. placed on labels or the outer surface of containers of medicaments to be dispensed from the dispensing system 140. It is contemplated that the machine readable codes on the medicament containers encode information such as the type of medication in the container, the mass, shape, dosage of each capsule and/or tablet, the expiration date of the medicament, etc. The codes are configured to be scanned and/or read by the scanning means and subsequently stored in a machine readable memory device incorporated within the dispensing system 140 such as, for example, a radio frequency identification ("RFID") tag or device that is present within the system for storing information related to the medicaments to be dispensed. Such a device is capable of wireless communication with other devices such as the processing device 120 or, alternatively, a computer or a wireless communication device reader in communication with the processing device 120.

In other embodiments, the scanning means is capable of counting the medicaments being dispensed and stores the exact inventory in the machine readable memory device which can be read by a wireless communication device reader within the dispensing system 140 or external to the dispensing system 140 and subsequently communicated to the processing device 120. Information from the wireless communication device can also be relayed or transmitted to one or more external computers or processing devices such as device 120 for monitoring the contents, operations, and status of the dispensing system 140.

The dispensing system 140 may also be configured to receive containers of medicaments via an adapter or adapters configured to accommodate various container or bottle sizes. The adapter may be, for example, a clamping or threaded coupling configured for releasable attachment to the dispensing system 140 on one end and to the medicament container or bottle on the other end. Alternatively, the adapter may be integrally formed on one end with the dispensing system 140 and configured to accommodate various container or bottle sizes on the other end. In embodiments, the coupling may be configured to puncture seal the cap of the container to facilitate hermetically sealed flow of medicaments from the container into the dispensing system 140. In this manner, the cap on the medicament need not be removed prior to being pre-supplied into the dispensing system 140.

The packaging system 150 is in communication with the dispensing system 140 and is configured for cooperative operation therewith. The packaging system 150 may be, for example, a blister packager as is well-known in the art, configured to substantially seal medication within the blister package 155 represented schematically in FIG. 1 and illustrated in an exploded view in FIG. 2. In use, the dispensing system 140 dispenses medication into recesses 170 (FIG. 2) formed in the blister package 155 for substantial sealing therein by the packaging system 150. It should be understood that the packaging system 150 may alternatively be incorporated within the packaging system 150 for integrated operation therewith.

Figure 2:
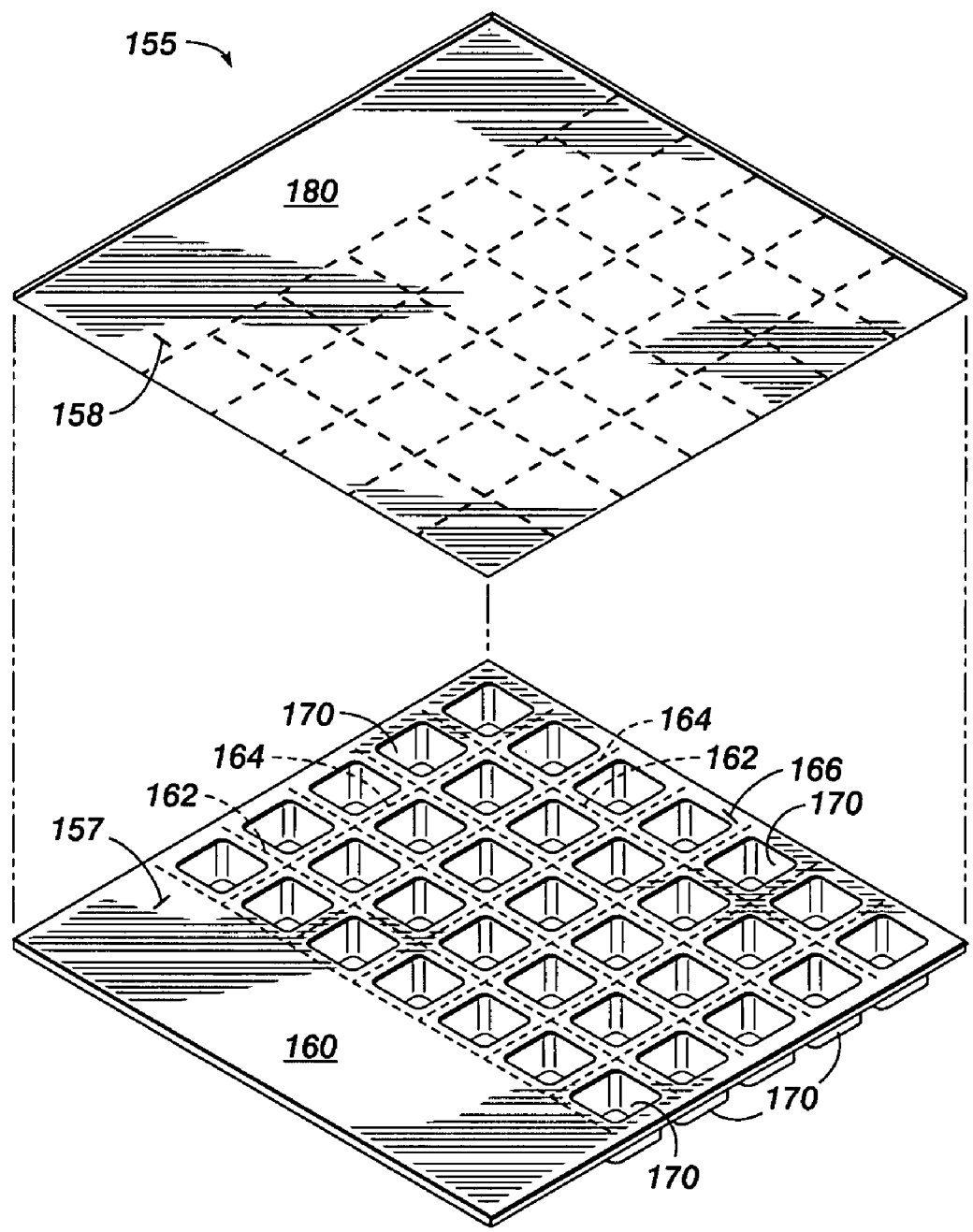
FIG. 2 shows an exploded view of the blister sheet and lidding sheet according to embodiments of the present disclosure.

FIG. 2 shows an exploded view of a blister package 155 according to embodiments of the present disclosure. The blister package 155 includes a blister sheet 160 having a plurality of recesses 170 formed therein and a lidding sheet 180. The blister sheet 160 is formed from a flat, clear plastic sheet of a suitable transparent thermoplastic polymer which has been thermoformed or die molded to form the pattern of blister recesses 170. The polymer must provide sufficient sealing properties to prevent the diffusion of unwanted moisture and oxygen in the blister recesses of the package 155 that may affect or deactivate the packaged medication. The lidding sheet 180 is made of frangible material, typically relatively thin and flexible metal foil or plastic, that has sealing properties like those discussed above to insure the hermetic preservation of medication sealed in the package. The blister recesses 170 are arranged in a plurality of columns and rows and are separated by substantially planar shoulder portions 164. The peripheral portions of the sheet 160 adjacent the edges of the sheet are also substantially flat and planar. As illustrated, score lines 162 are provided in the shoulder portions of the blister sheet 160 to form pre-weakened areas to facilitate separating the individual blisters from the package. This allows a patient's unused medications or blister recesses to be separated easily from the package and reused in other package assemblies.

The upper surface of the shoulder portions 164, including the peripheral portions 166, of the blister sheet 160 contain a coating 157 of a cohesive material. The coating can be applied by conventional methods and, alternatively, may be applied to the entire surface of the blister sheet 160. One entire surface of the lidding sheet 180 also bears a coating 158 of a cohesive material. The cohesive coating 158 on the lidding sheet 180 and the cohesive coating 157 on the blister sheet 160 can be the same or of different compositions. The cohesive coatings 157 and 158 serve to securely bond the blister sheet 160 to the lidding sheet 180 when the coated surfaces are positioned next to each other in the assembly of the package. Thus, the lidding sheet 180 serves to close the blister recesses 170 and encapsulate the medicaments therein.

Figure 3:
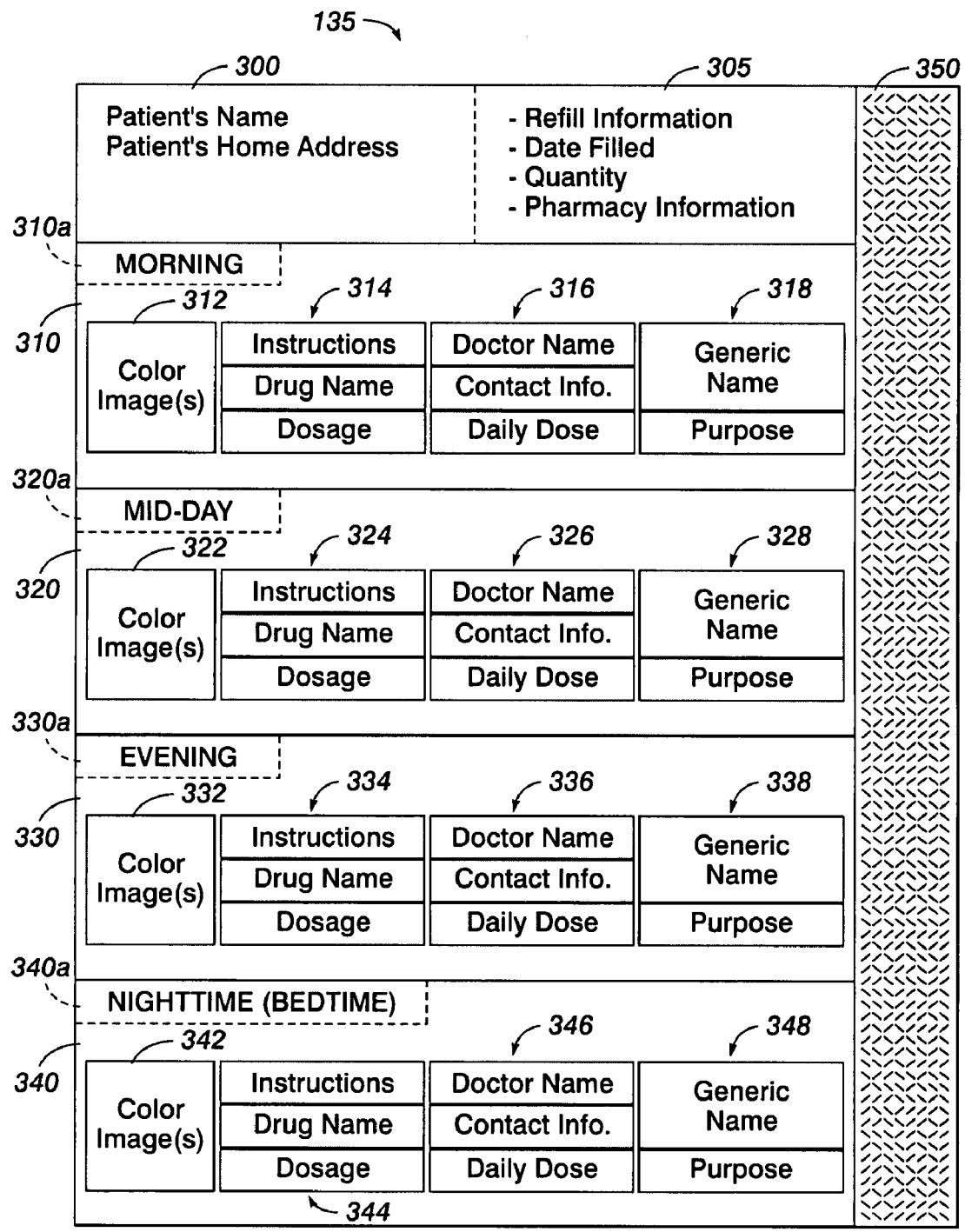
FIG. 3 shows a print of instructional data according to embodiments of the present disclosure.

In embodiments, the print 135 of instructional data relating to the packaged medicaments represented schematically in FIG. 1 and depicted in FIG. 3 may be applied to the rear surface of the lidding sheet 180 of the blister package 155 (not explicitly shown). The print 135 may be coated with an adhesive or glue material for adhering the print 135 to the lidding sheet 180. In further embodiments, the specific contents of each blister recess 170 may be set forth in matrix form that corresponds to the blister recesses 170 of the package 155 when the print 135 is applied to the lidding sheet 180. In use, a pharmacist may be provided with a kit to prepare and assemble the personalized package assembly, i.e., to couple the print 135 to the package 155 on an individual basis pursuant to an individual's prescription.

Referring now to FIG. 3, an exemplary print 135 of instructional data is shown which corresponds to medicaments sealed in the package 155 by the packaging system 155. A first information area 300 is shown at the top of the print 135 and may be printed with the patient's full name and home address below the patient's name. Information area 305 is also shown at the top of the print 135 and may be printed with general information about the medication such as the possible number of refills, the date the medication was dispensed, the quantity of tablets and/or capsules in the corresponding package 135, and information about the store or pharmacy including, for example, the prescription number, the pharmacy name, the pharmacy address and telephone number, etc. Additionally, information about the expiration date of the medicament may be included, for example, the date beyond which the medication may not be effective. As illustrated, information area 305 may be arranged adjacent information area 300 at the top of the print 135.

Below information areas 300 and 305 are information areas 310, 320, 330, and 340 which correspond to a particular time of day in which a patient is required to take a prescription medication. For example, information area 310a may be printed to indicate that any medication listed and/or illustrated in information area 310 are to be taken in the morning (e.g., with breakfast). Likewise, information areas 320a, 330a, and 340a may be printed to indicate that any medication listed and/or illustrated in information areas 320, 330, and 340 respectively, are to be taken at mid-day (e.g., with lunch), in the evening (e.g., with dinner), and at nighttime or bedtime (e.g., with a snack), respectively. For each information area 310, 320, 330, and 340, corresponding image areas 312, 322, 332, and 342 may be printed with images of any one or more prescription medications to be taken by the patient at that particular time of day. Typically, prescription medication is more easily identifiable by referencing the color of the outer coating of the tablet and/or capsule. Accordingly, the image areas 312, 322, 332, and 342 may be printed in color by printing system 130 (FIG. 1) to aid the patient in identifying specific prescription medication. Additionally, image areas 312, 322, 332, and 342 may include pictograms to distinguish generally, for example, between capsules and tablets.

Adjacent image areas 312, 322, 332, and 342 are information areas 314, 324, 334, and 344 respectively, which may contain information such as instructions for taking any prescription medication correspondingly illustrated in 312, 322, 332, and 342. Additionally, information areas 314, 324, 334, and 344 may have printed the identification or name of the medication or medications illustrated in image areas 312, 322, 332, and 342, respectively. The identification of the medication may be the trademarked name of the medication, if this version is prescribed, or the equivalent generic name if a generic is available and prescribed or dispensed. Further, information areas 314, 324, 334, and 344 may have the dosage for each medication identified in information areas 310, 320, 330, and 340, respectively, i.e., the strength or weight of the medication (10 mg, 20 mg, 100 mg, etc.).

Adjacent information areas 314, 324, 334, and 344 are information areas 316, 326, 336, and 346 respectively, which may contain information about the doctor prescribing the medication, including for example, his or her telephone number and optionally the address, the date the prescription is written and the doctor's DEA number. Additionally, the total daily allowable dose may be printed for each pill correspondingly identified in information areas 314, 324, 334, and 344. These information areas 316, 326, 336, and 346 can also include a warning not to take more than a specific number of capsules or tablets per day.

Adjacent information areas 316, 326, 336, and 346 are information areas 318, 328, 338, and 348 respectively, which may contain the equivalent generic name of the medication or medications identified in each information area 310, 320, 330, and 340, if the trademarked name version of the medication is prescribed, as discussed above with respect to information areas 314, 324, 334, and 344. In this way, the patient may be made aware of a generic alternative, if any, to the trademarked name version of the prescribed pill or pills. Additionally, information areas 318, 328, 338, and 348 may include a brief description of the purpose of the medication. A variety of purposes are designated for application by the printing system 130 (FIG. 1) and may include "anticoagulant", "sleep-aid", "blood pressure control", "anti-anxiety", "cough-cold", or the like.

A region 350 of encoded information which represents a structural description of the print 135, as well as other selected information, is also provided. The region 350 may be any suitable form of data encoding such as, for example, a bar code, a data glyph, or the like. The encoded information contained in the region 350 may include the complete description of the location of the information areas or fields on the print 135. Thus, if the location of any of the information areas or fields changes from one print to the next, the data in the region 350 may be updated to accurately describe the new position of the information areas or fields. Of course, the region may be arbitrarily located on the print 135.

Figure 4:
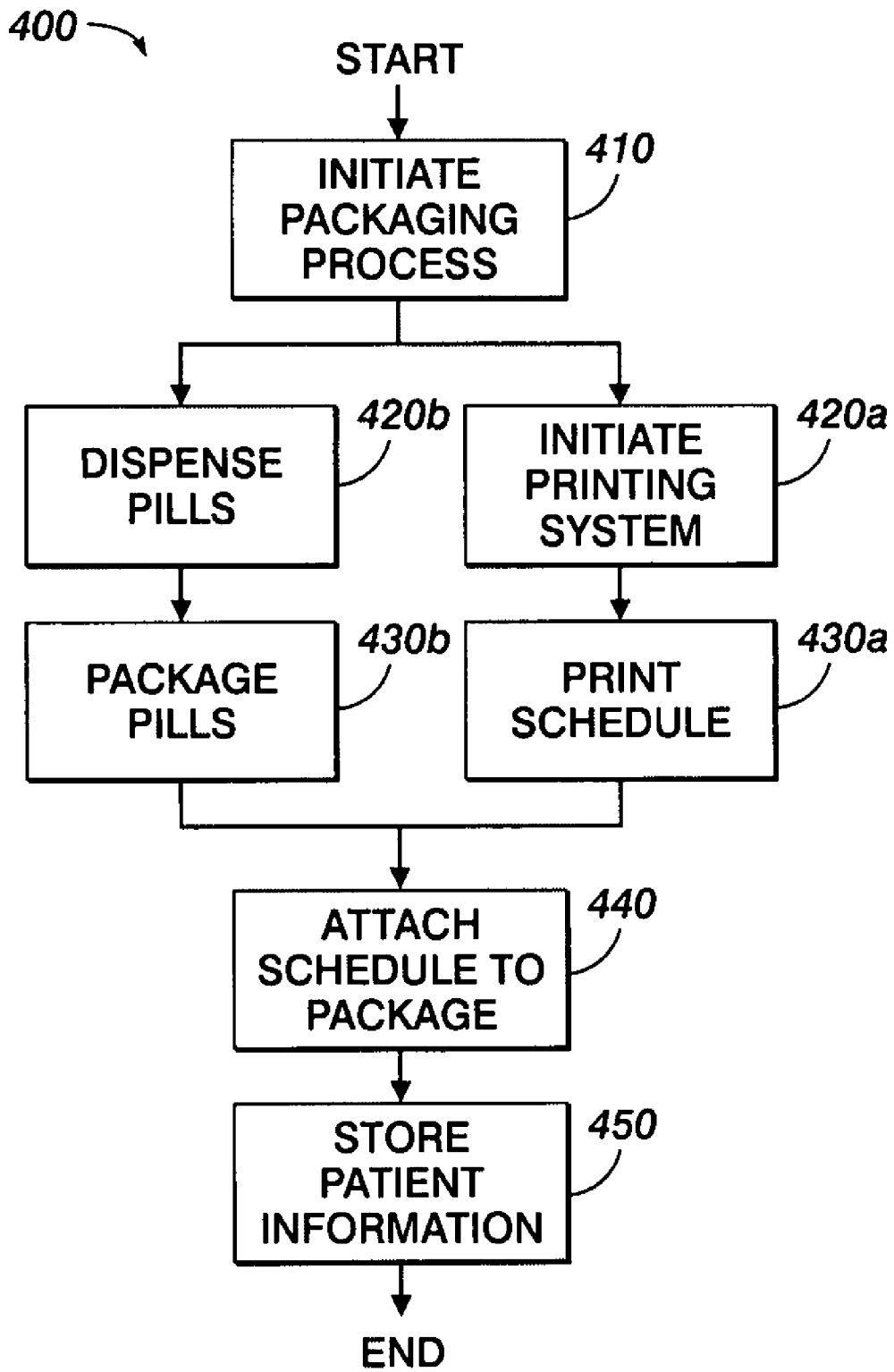
FIG. 4 shows a process for personalized packaging of medicaments according to embodiments of the present disclosure.

Operation of the system 100 for generating a personalized package of medication is described with reference to the process 400 shown in FIG. 4. At the step 410, a pharmacist initiates the packaging process by inputting prescription data from a patient including, for example, the name, address, and/or phone number of the patient into the processing device 120 through the user interface 110. In response, the CPU 150 communicates the prescription data to both the printing system 130 and the dispensing system 140. In the step 420b, the dispensing system 140 dispenses the medication corresponding to the prescription data received from the CPU 150. For example, the patient data may be a prescription for a certain dosage and/or quantity which the dispensing system 140 interprets and dispenses accordingly. In a substantially simultaneous manner, the printing system 130 is initiated with the prescription data communicated from the CPU 150 in step 420a for generating the print 135 of instructional data to correspond to the prescription dispensed in step 420b. The dispensed prescription is packaged by the packaging system 150 in the step 430b resulting in the package 155. In a substantially simultaneous manner, the print 135 of instructional data corresponding to the packaged prescription in package 155 is printed by the printing system 130 in the step 430a.

In the step 440, the print 135 of instructional data may be coupled to the package 155 in a variety of ways including, for example, attachment to the lidding sheet 180 via a cohesive coating (discussed above), taped, stapled, clipped, or even by simply placing the print 135 and package 155 together in an additional package or bag, i.e., the print 135 and package 155 need not be actually and/or physically mated to one another.

In the step 450, the prescription data and/or patient data entered into the user input 110 as well as the results of the completed packaging process 400 are stored in the memory 122. The packaging process 400 then ends.

It will be appreciated that variations of the above-disclosed and other features and functions, or alternatives thereof, may be desirably combined into many other different systems, methods and/or applications. Also that various presently unforeseen or unanticipated alternatives, modifications, variations or improvements therein may be subsequently made by those skilled in the art which are also intended to be encompassed by the following claims.

The invention claimed is:

1. A method of packaging medication comprising:
   generating input data related to the medication to be packaged through a user interface in communication with a processing device, wherein the processing device includes a CPU configured to process the input data received from the user input;
   dispensing the medication from a dispensing system in bilateral communication with the processing device, the dispensing system being configured to receive the user input from the CPU, wherein the medication dispensed is based on the user input, said system having scanning means for reading machine readable data and for counting medicaments being dispensed by said dispensing system;
   generating a print of instructional data from a printing system in communication with the processing device, the printing system being configured to receive the user input from the CPU, wherein the print of instructional data is based on the user input, wherein the steps of dispensing the medication and generating the print of instructional data are performed substantially simultaneously; and
   packaging the dispensed medication through a packaging system in communication with the dispensing device, the packaging system being configured to package the medication dispensed from the dispensing system.

2. The method according to claim 1, further comprising the step of mating the print of instructional data to the packaging.

3. The method according to claim 1, wherein the packaging is a blister package.

4. The method according to claim 1, further comprising the step of pre-formatting the print of instructional data through the user interface.

5. The method according to claim 1, wherein the print of instructional data further includes encoded data related to the layout of the instructional data on the print.

6. The method according to claim 1, wherein the packaging further includes a coating of cohesive for mating the print of instructional data thereto.

7. The method according to claim 1, wherein the processing system communicates with at least one of the user interface, the dispensing system and the printing system in a networked configuration.

8. The method according to claim 1, wherein the packaging system is integrated within the dispensing system.

9. A system for personalized packaging of medication comprising:
   a processing device having a CPU and a user interface, the user interface being configured to receive input data related to at least one type of medication to be packaged, wherein the user interface communicates the input data to the CPU for processing;
   a dispensing system in communication with the processing device, wherein the dispensing system is configured to be pre-supplied with the at least one type of medication and to dispense the at least one type of medication based on the input data communicated from the CPU to the dispensing system, said system having scanning means for reading machine readable data and for counting medicaments being dispensed by said dispensing system;
   a printing system in communication with the processing device and configured to generate a print of instructional data based on the input data communicated from the CPU to the printing system, wherein the print of instructional data includes data correspondingly related to the at least one type of medication dispensed by the dispensing system; and
   a packaging system in communication with the dispensing system and configured to seal the at least one type of medication dispensed from the dispensing system within the personalized packaging.

10. The system according to claim 9, wherein the dispensing system is configured to dispense the at least one type of medication into the packaging for sealing by the packaging system.

11. The system according to claim 9, wherein the packaging is a blister package.

12. The system according to claim 9, wherein the processing system is at least one of an electronic planner and a computer.

13. The system according to claim 9, wherein the dispensing system further includes scanning means for monitoring information related to the medication to be dispensed.

14. The system according to claim 9, wherein the processing system communicates with at least one of the dispensing system and printing system over a network.

15. The system according to claim 9, wherein the user interface communicates with the processing device over a network.

16. The system according to claim 9, wherein the at least one type of medication is pre-supplied in a container-form configured for attachment to the dispensing system.

17. The system according to claim 9, wherein the personalized package is configured for mated relation to the print of instructional data.

18. The system according to claim 9, wherein the print of instructional data includes information related to the at least one type medication and at least one of a color image of the at least one type of medication, dosage information related to the least one type of medication, and the purpose of the at least one type of medication.

19. The system according to claim 9, wherein the system for personalized packaging substantially simultaneously counts and dispenses the at least one type of medication, and prints the print of instructional data.

20. A system for personalized packaging of medication comprising:
   a processing device having a user interface, the user interface being configured to receive input data related to at least one container of medication to be packaged, the at least one container of medication including machine readable data related to the medication encoded thereon for monitoring by the processing device;
   a dispensing system having a machine readable memory device in communication with the processing device, wherein the dispensing system is configured to be pre-supplied with the at least one container of medication and to dispense the at least one container of medication based on the input data communicated from the processing device to the dispensing system, the dispensing system further including scanning means for reading the machine readable data and for counting medication being dispensed, wherein the machine readable data is stored in the machine readable memory device for communication to the processing device;

a printing system in communication with the processing device and configured to generate a print of instructional data based on the input data communicated from the processing device to the printing system, wherein the print of instructional data includes data correspondingly related to the at least one container of medication dispensed by the dispensing system; and a packaging system in communication with the dispensing system and configured to seal the medication from the at least one container of medication dispensed from the dispensing system within the personalized packaging, wherein the personalized packaging is configured for mated relation to the print of instructional data.

21. The system according to claim 20, wherein the machine readable memory device is an RFID device.

22. The system according to claim 20, wherein the scanning means substantially simultaneously counts and dispenses medication, and prints the print of instructional data.

* * * * *